Figure 1:
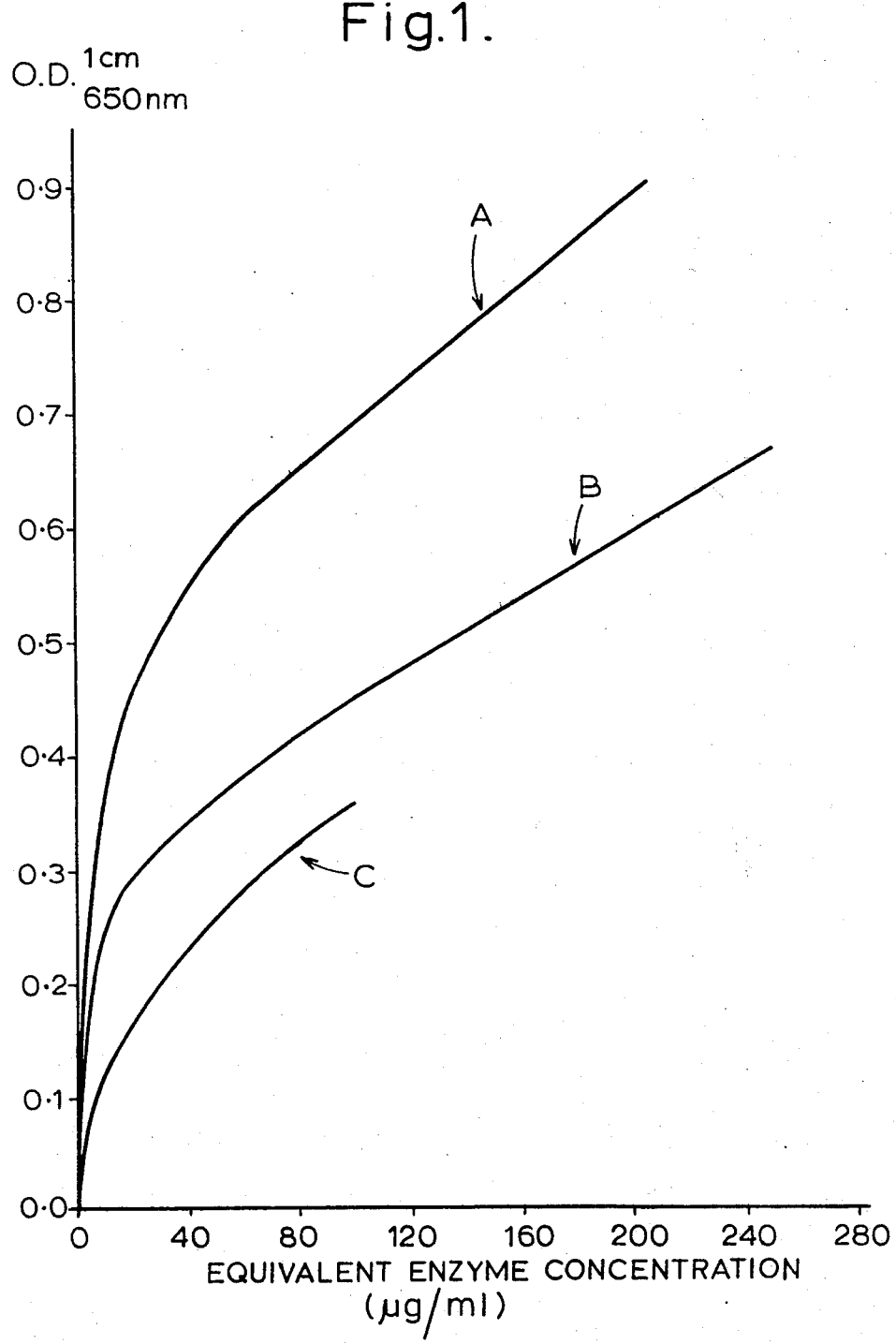

United States Patent [19]

Green et al.

[11] 4,055,635

[45] Oct. 25, 1977

[54] FIBRINOLYTIC COMPOSITIONS

[75] Inventors: Joseph Green, London; Michael Anthony Cawthorne, Horsham, both of England

[73] Assignee: Beecham Group Limited, England

[21] Appl. No.: 485,302

[22] Filed: July 2, 1974

[30] Foreign Application Priority Data

July 5, 1973  United Kingdom ............... 32071/73

[51] Int. Cl.$^2$ ..................... A61K 31/74; A61K 37/48
[52] U.S. Cl. ........................................ 424/78; 424/94; 195/DIG. 11
[58] Field of Search ................................. 424/94, 78; 195/DIG. 11

[56] References Cited

U.S. PATENT DOCUMENTS

| 2,908,614 | 10/1959 | Muggleton et al. | 424/94 |
|---|---|---|---|
| 3,019,171 | 1/1962 | Bloch et al. | 424/94 |
| 3,576,760 | 4/1971 | Gould et al. | 424/32 |
| 3,616,229 | 10/1971 | Wildi et al. | 195/DIG. 11 |
| 3,625,827 | 12/1971 | Wildi et al. | 195/DIG. 11 |
| 3,639,213 | 2/1972 | Ginger et al. | 424/94 |
| 3,654,083 | 4/1972 | Moelker | 195/DIG. 11 |
| 3,691,090 | 9/1972 | Kitajima et al. | 424/32 |
| 3,876,501 | 4/1975 | Hanushewsky | 195/DIG. 11 |

*Primary Examiner*—Sam Rosen
*Attorney, Agent, or Firm*—Jacobs & Jacobs

[57] ABSTRACT

Fibrinolytic pharmaceutical compositions are provided in unit dosage form and comprise a water-soluble complex of a proteolytic enzyme linked covalently to a polymeric substance.

9 Claims, 2 Drawing Figures

FIBRINOLYTIC COMPOSITIONS

This invention relates to certain pharmaceutical compositions, in particular to fibrinolytic compositions in unit dosage form.

A proteinaceous material known as fibrinogen is present in blood. Under the action of one or more enzyme this is converted into fibrin which forms the matrix of blood clots unless these clots are rapidly broken down or lysed by the further action of fibrinolytic enzymes. It is believed that this lysing of fibrin may be effected by an enzyme plasmin which it itself liberated by some enzymatic action from a proteinaceous material, plasminogen, itself present in the blood. Thus blood normally contains both fibrinogen and plasminogen and the latter breaks down by the action of an activator to produce plasmin. The plasmin so liberated is then able to effect lysis of the clot-forming fibrin formed as the result of breakdown of the fibrinogen. The breakdown products of the fibrin are peptides soluble in blood and so the blood clots are dispersed.

In thrombosis and related diseases one or more of these stages is rendered ineffective and much research has been carried out to elucidate the cause of the disease and to accelerate the breakdown of fibrin blood clots that may be formed; that is to produce fibrinolytic pharmaceutical compositions.

Plasmin is a proteolytic enzyme and its specificity is not unrelated to that of certain other proteolytic enzymes. Such a proteolytic enzyme could interact with the fibrinolytic system at three positions; that is (a) it could degrade fibrinogen to fibrin thereby causing clots to form; (b) it could lyse fibrin to soluble peptide products; and (c) it could activate plasminogen to form plasmin which would effect the desired lysis of the fibrin. This last mentioned reaction is believed to involve the cleavage of a single arginylvalyl bond and an enzyme which effects this cleavage is herein referred to as having peptidolytic activity. Such activity may be determined in terms of the esterolytic activity of the enzyme towards low molecular weight substrates and is conveniently measured spectrophotometrically using synthetic substrates such as benzoyl arginine ethyl ester or tosyl arginine methyl ester. Such peptidolytic activity, which is desirable in promoting the desired liberation of plasmin, is to be separated from general proteolytic activity, which is not desired since it can lead to uncontrolled proteolytic degradation in vivo. Such general proteolytic activity can be demonstrated by the hydrolysis of pure proteins such as casein, such activity being herein referred to as caseinolytic activity.

Two proteins alleged to possess fibronolytic activity are currently available. However, they have disadvantages. Thus streptokinase is antigenic and even the purified enzyme cross-reacts with antibodies raised by the patient against streptococcal infections. Thus, before effective therapy can commence, the antibody titre must be neutralised. Moreover, while streptokinase is believed to work as a plasminogen activator, it does not itself have any peptidolytic or esterolytic activity. Its activity may be due to the formation of a complex between the streptokinase and plasminogen and/or plasmin, which complexes are able to act as direct activators of further amounts of plasminogen. The second available fibrinolytic enzyme is urokinase. While this is not antigenic, it is very expensive and is currently only available by isolation in small quantities from human urine. Its mode of action is believed to be that of a plasminogen activator.

It is therefore an object of the present invention to find enzyme systems with fibrinolytic and/or plasminogen activation (peptidolytic) activity, but with low caseinolytic activity. We have discovered that the formation of water-soluble complexes of proteolytic enzymes linked to polymeric substances can lead to the desired properties.

Such water-soluble enzyme complexes have been previously described in the literature, but their use for the purposes of medical treatment does not appear to have been previously contemplated, particularly not for purposes where the complex is to be injected into the blood stream as it needs to be for the rapid in vivo dispersal of blood clots.

Accordingly, the present invention provides a fibrinolytic pharmaceutical composition in unit dosage form which comprises a water-soluble complex of a proteolytic enzyme linked covalently to a polymeric substance.

For purposes of plasminogen activation activity, the proteolytic enzyme employed is preferably trypsin, due to its correct peptidase specificity, but the use of similar enzymes, for example chromotrypsin, bromelain, and papain is also possible from the point of view of direct fibrinolytic activity. There may also be employed complexes prepared from proteolytic enzymes commercially available, for example pronase, a broad-spectrum proteolytic enzyme, isolated for *Streptomyces griseus;* and brinase, which is isolated from *Asperigillus oryzae.* Both of these have fibrinolytic and plasminogen activiation activity.

The polymeric substance is preferably one that is water-soluble and digestable by in vivo processes. Thus it is preferred to use polysaccharides such as dextran, dextrins, cellulose, or starch. Dextrans are preferred, especially those having a molecular weight in the range 10,000–500,000, for example those desginted as T40 and T70. designated Such polysaccharides may, if desired, be one that has been modified by reaction with modifying agents, e.g. epichlorhydrin or it may be carboxymethyl-, hydroxyethyl or aminoethyl- modifed cellulose or a partially degraded starch. It is also possible to link the enzyme to a water-insoluble polymeric substance such as cross-linked dextran, and then render the resulting complex water-soluble by appropriate degradation process, e.g. by partial hydrolysis or by reaction of a cross-linked dextran with dextranase.

It has further been found particularly suitable to use for the purposes of the present invention polymers that are modified saccharides or oligosaccharides, such as sucrose, dextrose or lactose. An especially useful polymer of this type is one that is commercially available under the Trade Name "FICOLL", which is a sucroseepichlorhydrin copolymer. A FICOLL polymer with a molecular weight of about 400,000 has been found to be suitable.

It is also possible to use synthetic water-soluble polymers, such as polymers of polyvinylalcohol and copolymers of maleic or acrylic anhydrides with ethylene, styrene, methyl vinyl ether, divinyl ether or vinyl acetate. Such polymers are, for example, described in West German Offenlegungschriften Nos. 1,948,177 and 1,948,298 and in British patent specifications Nos. 1,290,701 and 1,223,281.

One suitable range of water-soluble copolymers are the methyl vinyl ether/maleic anhydride copolymers sold under the Trade Name "GANTREZ AN", particularly "GANTREZ AN 119" (a copolymer of molecular weight about 250,000). The maleic anhydride copolymers may be reacted with the proteolytic enzyme by any of the general methods described in British Pat. No. 1,290,701. For example the enzyme may be reacted with a GANTREZ AN polymer in the presence of a strong buffer solution or other means of maintaining a neutral pH.

The water-soluble enzyme complexes for present use may be prepared by any of the known methods for linking enzymes to polymers provided that the resulting complex can be regarded as water-soluble. By the use herein of the term "water-soluble", we include reference to materials that are dispersible in water to yield colloidal solutions. In such cases the particles should have diameters less than $2\mu$. Such linking methods are described, for example in British Pat. No. 1,325,912 and include coupling the proteolytic enzyme to the polymer by the use of such reagents as cyanogen halides, particularly cyanogen bromide; s-triazines, particularly 2-amino-4,6-dichloro-s-triazine; acyl-azides, diazonium compounds, for example 2-hydroxy 3-(p-diazophenyl) propyl ether; organic cyanates such as phenyl cyanate and diorganocarbodiimides. Often such linking agents are used first to react with the polymer and provide reactive groups on the same, which groups are then caused to react with the enzyme. In some cases the enzymes may react with the polymer, for example if this contains, or has been modified to contain, certain active groups such as anhydride linkages, aminoethyl, hydroxyethyl or carboxymethyl substituents. Dialdehydes, such as glutaraldehyde and glyoxal can also be used to form bridges between the enzyme and the polymer, provided the latter contains free amino groups. To lengthen these bridges, aliphatic diamines can be used in addition to dialdehyde.

The enzyme is linked to the polymer in an amount such that the weight ratio of polymer:enzyme is within the range 0.1:1 to 100:1, preferably from 2:1 to 50:1.

It is most desirable that the water-soluble enzyme complex prepared by any of the methods described above should then be purified so that it is substantially free from the unreacted enzyme. This is because, as above stated, the free proteolytic enzyme will often have undesirable reactions in vivo, for example it may induce allergic reaction by reaction with antibodies present in the blood of the patient. Such purification is preferably carried out using physical separation methods which separate chemicals based on differences in molecular size, because the enzyme complex will have a molecular weight that is much larger than the free enzyme. Indeed, preferably the enzyme will be complexed with a polymer having a molecular weight of from 10,000 to 500,000. Thus the enzyme complexes for present use have preferably been subjected to ultrafiltration or gel filtration which results in the removal therefrom of the free enzyme which has a much lower molecular weight than the complex. A further purification may then be carried out using dialysis.

Moreover, if the free enzyme is one likely to form harmful antibodies, the crude enzyme complex may be passed through a column containing the specific antibody reactive to the free enzyme, wherein such antibody has been previously immobilised on a support such as Sephadex or agarose. The free enzyme, but not the enzyme complex, reacts with the immobilised antibody whereas the enzyme complex passes through the column and is therefore purified as desired.

The enzyme complexes for present use are preferably sterilised by passing through Seitz filters and are then desirably obtained in a freeze-dried, i.e. lyophilised, state.

It is likely that the complexes of this invention have the following advantages over the corresponding uncomplexed enzyme:

a. an increased biological half-life; and/or
b. a lower degree of plasma inhibition: and/or
c. a lower degree of antigenicity.

The pharmaceutical compositions are in unit dosage form, that is they contain a predetermined amount of the enzyme complex. Preferably this amount is indicated in activity units so that the doctor can prescribe the appropriate dose dependent on the degree of fibrinolysis which he desires to achieve in the patient, this partly depending on the extent to which he judges there has been undue formation of fibrin clots in the patient's blood. Thus the compositions of the invention are preferably presented in sealed ampoules containing a predetermined amount of sterile freeze-dried enzyme complex.

For use, the fibrinolytic compositions of the invention are to be prepared in a form adapted for injection, either in the form as sold or more usually after dissolution in an appropriate solvent. Thus, preferably the aforesaid sealed ampoule will be taken and broken and the contents thereof dissolved or suspended in sterile or pyrogen-free water or isotonic saline for administration by injection into the blood stream of the patient to be treated. Alternatively, the unit dosage forms of the invention may consist of pre-prepared ampoules of solutions of the said enzyme complex of predetermined concentration in water or isotonic saline. The compositions of the invention are therefore formulated in a fundamentally different manner to the mouth wash compositions described in German Offenlegungschrift No. 1,948,298 because such compositions are not suitable for injection or for conversion into injectable compositions and they do not contain a predetermined dose of the enzyme complex.

The efficacy of some of the enzyme complexes for the compositions of the invention is illustrated by the following Examples.

EXAMPLE 1

Preparation of Water-soluble Enzyme Complex of Trypsin on Gantrez

Gantrez AN-119 (a methyl vinyl ether-maleic anhydride copolymer having a molecular weight of 250,000) (10 g) was added to 300 ml of 0.2M phosphate pH 7.4 buffer and the mixture was stirred for about 5 mins. to produce a suspension. A solution of trypsin (1 g) in phosphate buffer (40 ml) was added and the mixture was mechanically stirred for 24 hours at 4° C. The resulting solution after considerable dilution with deionised water was purified by repeated ultrafiltration through a membrane that had a molecular weight cut-off or 300,000. By this means free unreacted tryosin, which passed through the membrane was separated from the adduct, which was retained in the ultrafiltration cell. This process also served to remove the phosphate buffer from the adduct and this was further accomplished by dialyzing the adduct against deionised water. The adduct was finally freeze-dried to yield 8.9 g of a white fluffy product. The protein content of the adduct was determined by the method of Lowry et al, using trypsin as standard, and was found to be 47 μg/mg.

The peptidolytic activity of the adduct was measured by its esterolytic ability to release N-benzoyl arginine from N-benzoyl arginine ethyl ester. Using this assay each mg of the adduct had an activity equivalent to 125 μg of trypsin, therefore the adduct had a greater esterolytic activity and therefore a greater peptidolytic activity/82 g protein than free trypsin.

The caseinolytic activity of trypsin and the adduct were measured by the method of Remmert & Cohen, J. Biol. Chem, 181, 431–448, (1949). Each mg of adduct had an activity equivalent to 10 μg of enzyme and therefore the caseinolytic activity of the adduct was reduced relative to the activity of free trypsin.

The fibrinolytic activities of trypsin and the adduct were measured by their ability to lyse plasma clots. Human plasma containing a trace of $I^{125}$-fibrinogen was clotted with thrombin. The clots were then incubated in a solution of the enzyme or adduct and the release of $I^{125}$ products from the clot into the medium was measured, (Table 1). The adduct was relatively much more active than free trypsin; each mg of adduct being the equivalent of 320 μg trypsin.

Table 1.

| Comparison of Trypsin and Trypsin-Gantrez | | |
|---|---|---|
| Assay | Trypsin equivalent | Ratio |
| Protein content | 47 μg/mg | 1 |
| Esterolytic cleavage of N-benzoyl arginine ethyl ester | 125 μg/mg | 2.5 |
| Fibrinolysis of plasma clot | 300 μg/mg | 7.0 |
| Caseinolytic test | 10 μg/mg | 0.2 |

Thus it will be noted that the water-soluble enzyme complex had fibrinolytic activity that was 7 times that of the free enzyme and an esterolytic activity 2.5 times that of the free enzyme, but a caseinolytic activity that was only one-fifth that of the free enzyme. Thus the desired combination of properties, as stated aforesaid, is shown to have been achieved.

EXAMPLE 2

Trypsin/Dextran T40 Complex (I)

Dextran T40 (average molecular weight = approx. 40,000, measured by gel filtration) (1 g) was dissolved in 10 ml 0.1 M sodium bicarbonate buffer (pH 9.0). 1 g of cyanogen bromide was dissolved in water (30 ml) and was added to the dextran solution. The mixture was maintained at room temperature and was stirred for 10 minutes during which time the pH was maintained constant at pH 9 by the addition of 2M NaOH. After 10 minutes the reaction mixture was added to 200 ml acetone, whereupon the cyanogen bromide activated dextran was precipitated. The precipitate was filtered and then air-dried to yield a fine powder that was freely soluble in water.

103 mg of the cyanogen bromide activated dextran T40 was then reacted with 98 mg of trypsin by mixing solutions of the two substances in bicarbonate buffer (pH 9.0). The mixture was slowly rotated at 4° C for 16 hours. The trypsin-dextran adduct was separated from free trypsin by chromatography on a Sephadex G-75 column. The trypsindextran adduct was obtained, after lyophilisation, as a fluffy white powder and weighed 22.5 mg.

The adduct had a protein content equivalent to 22 μg trypsin per mg of adduct. It fibrinolytic activity was compared with that of trypsin by measuring the ability of solutions of each to cause the release of radioactivity, during a 10 minute incubation period, from thrombininduced plasma clots, which had been tagged with $I^{125}$-fibrinogen (Table 2).

Table 2.

| Effect of Trypsin and Trypsin-dextran on fibrinolysis in vitro | | |
|---|---|---|
| | | $I^{125}$-released/10 min. incubation (disintergration) |
| Blank | | 1089 |
| Trypsin | 40 μg/ml | 1737 |
| | 70 μg/ml | 2184 |
| | 100 μg/ml | 2279 |
| | 150 μg/ml | 2689 |
| | 200 μg/ml | 3081 |
| Trypsin-dextran | 500 μg/ml (equiv.11 μg trypsin/ml) | 993 |
| | 1000 μg/ml (equiv.22 μg trypsin/ml) | 2114 |
| | 2000 μg/ml (equiv.44 μg trypsin/ml) | 5094 |

The trypsin-dextran adduct had a 2.5 times greater fibrinolytic activity on a protein basis than free trypsin for 2 mg of the adduct contains approximately equivalent protein to 40 μg trypsin.

EXAMPLE 3

Pronase-Dextran T40 (I)

Dextran (molecular weight 40,000) 6 g was dissolved in water (600 mls) and adjusted to pH 11,00 with 2N sodium hydroxide. Cyanogen bromide (1.8 g) was added and further sodium hydroxide added to maintain the pH at 11.00 until reaction ceased. The solution was then adjusted to pH 8.5 with 2N hydrochloric acid. 200 ml of the solution was mixed with Pronase (200 mg) and stirred at 4° C for 16 hours. The product was ultrafiltered using a membrane retaining material of M.W. above 10,000, to a volume of approximately 5 ml. Lyophilisation of this solution gave 2.114 g of a white powder. 1 gram of this powder was purified by gel filtration on a 3 × 40 cm Sephadex G-100 column equilibrated and eluted with 0.1 M sodium phosphate buffer, pH 7.0. Protein-containing fractions eluting before the free Pronase were pooled, ultrafiltered (as above) to a volume of 10 ml and lyophilised to give 0.88 g of a white powder.

The protein content of this material was 32 μg Pronase per mg of adduct.

The fibrinolytic activity of the material was measured by the release of radioiodinated peptides from $^{125}I$-fibrinogen - containing human plasma clots as described previously. By the use of anticoagulated human plasma in place of buffer in the external medium, the plasma inhibition of fibrinolytic enzymes may be assessed (Table 3).

Table 3.

| Effect of Pronase and Pronase-dextran T40 (I) on Fibrinolysis in vitro | | |
|---|---|---|
| | D.P.M. Released (30 min.incubation in buffer) | D.P.M. Released (30 min.incubation in plasma) |
| Blank | 732 (2.4) | 683 (2.2) |
| Pronase 20 μg/ml | 1757 (5.8) | 962 (3.2) |
| 50 μg/ml | 3171 (10.5) | 1020 (3.4) |
| 100 μg/ml | 7624 (25.4) | 1101 (3.6) |
| Pronase-dextran | | |

Table 3.-continued

| Effect of Pronase and Pronase-dextran T40 (I) on Fibrinolysis in vitro | | |
|---|---|---|
| | D.P.M. Released (30 min.incubation in buffer) | D.P.M. Released (30 min.incubation in plasma) |
| 8 μg/ml (Pronase equivalent) | 1279 (4.2) | 1243 (4.1) |
| 16 μg/ml | 1621 (5.4) | 1916 (6.4) |
| 32 μg/ml | 2180 (7.0) | 1916 (6.4) |
| 64 μg/ml | 3082 (10.2) | 2459 (8.2) |

(Figures in parentheses indicate percentage release of total $^{125}$I).
[D.P.M. = Disintegrations per minute]

Table 4.

| Effect of pronase-dextran on Fibrinolysis in vitro in the presence of added plasminogen | | |
|---|---|---|
| | D.P.M. RELEASED. 30 MIN INCUBATION IN BUFFER IN THE PRESENCE OF PLASMINOGEN AT: | |
| | 0.4 Casein units/ml | 1.6 Casein units/ml |
| Blank | 1252 (4.1) | 1163 (3.8) |
| Pronase-dextran 8 μg/ml (Pronase equivalent) | 1624 (5.3) | 1664 (5.4) |
| 16 μg/ml | 2031 (6.6) | 4323 (14.1) |
| 32 μg/ml | 3305 (10.8) | 5953 (19.5) |
| 64 μg/ml | 4173 (13.6) | 9221 (30.1) |

(Figures in parentheses indicate percentage release of total 125I)

The caseinolytic activity of the preparation measured in Example 10 is approximately equal to that of the equivalent amount of unmodified free Pronase. There is, however, an apparent increase in the esterolytic activity of the complex (Example 9). In this preparation, the effect of attaching Pronase to dextran has been to produce a material with essentially the same caseinolytic activity abd fibrinolytic activity in buffer as free Pronase, but with a greater reduced inhibition of fibrinolytic activity by plasma. The effect of exogenous plasminogen on fibrinolysis by the conjugate shows that the material is capable of acting as a plasminogen activator (Table 4).

EXAMPLE 4

Trypsin-Dextran T40 (II)

Dextran (M.W. 40,000) (1 g) was dissolved in water (100 ml) and activated with cyanogen bromide (0.5 g) at pH 11.0 as described previously. The pH of the solution was adjusted to 8.5 and trypsin (200 mg) and benzamidine hydrochloride (100 mg to inhibit autolysis) added. The solution was stirred at 4° C for 16 hours and then ultrafiltered (membranes as before) to a volume of 10 ml. The material was purified on a Sephadex G-100 column as before. Pooled fractions containing conjugate were ultrafiltered and lyophilised to give a white power (1.16 g) containing 126 μg protein/mg adduct. Fibrinolytic activity is shown in Table 5.

Table 5.

| Fibrinolytic activity of trypsin and trypsin-dextran T40 (II) in vitro | | |
|---|---|---|
| | D.P.M. Released (30 min.incubation in buffer) | D.P.M. Released (30 min.incubation in plasma) |
| Blank | 778 (2.20) | 1114 (3.1) |
| Trypsin 25 μg/ml | 2125 (6.0) | — |
| 50 μg/ml | 4554 (12.8) | — |
| 75 μg/ml | 4064 (11.4) | — |
| 100 μg/ml | 7665 (21.6) | 1166 (3.3) |
| 500 μg/ml | — | 1206 (3.4) |
| 750 μg/ml | — | 1358 (3.8) |
| Blank Trypsin-dextran T40 (Trypsin equivalent) | 1110 (3.6) | 885 (2.8) |

Table 5.-continued

| Fibrinolytic activity of trypsin and trypsin-dextran T40 (II) in vitro | | |
|---|---|---|
| | D.P.M. Released (30 min.incubation in buffer) | D.P.M. Released (30 min.incubation in plasma) |
| 30 μg/ml | 1517 (4.9) | — |
| 63 μg/ml | 1462 (4.7) | 1006 (3.2) |
| 126 μg/ml | 1937 (6.2) | 1084 (3.5) |
| 252 μg/ml | 4836 (15.5) | 1280 (4.1) |

(Figures in parentheses indicate percentage release of total $^{125}$I)

The caseinolytic activity of the conjugate is shown in FIG. 1 and is approximately 60% of that of free trypsin. In this example, the reduction of caseinolytic activity on attachment to dextran is paralleled by a reduction of fibrinolytic activity and there is retention of inhibition by plasma. Esterolytic activity, however, is increased (Example 9).

EXAMPLE 5

Chymotrypsin-Dextran T40

Dextran (M.W. 40,000) (1 g) was dissolved in water (100 ml) and mixed with cyanogen bromide (0.5 g) at pH 11.00 as described previously. After complete reaction, the pH was adjusted to 8.5 using 2N HCl and 0.5M sodium bicarbonate. Chymotrypsin (200 mg) and benzamidine hydrochloride (200 mg) were added and the solution stirred at 4° C for 16 hours. The solution was ultra-filtered (membrane as before) to a volume of 5 ml and then purified on a Sephadex G-100 column as previously described. Pooled fractions containing conjugate were concentrated by ultrafiltration and lyophilised. This yielded 1.56 g of a white powder containing buffer salts and with a protein content of 73 μg/mg. Fibrinolytic activity is shown in Table 6.

Table 6.

| Fibrinolytic activity of Chymotrypsin and Chymotrypsin-Dextran T40 in vitro | |
|---|---|
| | D.P.M. Released (30 min.incubation in buffer) |
| Blank | 1264 (2.43) |
| Chymotrypsin 20 μg/ml | 1675 (3.22) |
| 50 μg/ml | 2828 (5.44) |
| 100 μg/ml | 4384 (8.44) |
| 200 μg/ml | 10801 (20.80) |
| Chymotrypsin-Dextran T40 (Chymotrypsin equivalent) 14.6 μg/ml | 1544 (2.97) |
| 36.5 μg/ml | 1664 (3.20) |
| 73.0 μg/ml | 1839 (3.54) |
| 146.0 μg/ml | 2855 (5.49) |

(Figures in parentheses indicate percentage release of total $^{125}$I)

Caseinolytic activity of the conjugate (FIG. 2) is approximately 50% of that of free enzyme and, as in Example 4, parallels the (reduced) fibrinolytic activity.

EXAMPLE 6

Trypsin-Ficoll

Ficoll (M.W. 400,000) (1 g) was dissolved in water (100 ml) and activated with cyanogen bromite (0.5 g) at pH 11.00 as described previously. The pH of the solution was adjusted to 8.5 and trypsin (100 mg) and benzamidine hydrochloride (100 mg) added. After stirring at 4° C for 16 hours, the solution was ultrafiltered and purified by gel filtration as described above. The product after ultrafiltration and lyophilisation was a white powder, 0.89 g, containing 73 μg protein/mg. Fibrinolytic activity is shown in Table 7.

Table 7.

| Fibrinolytic activity of Trypsin-Ficoll in vitro (for trypsin activity see Example 4) | | |
|---|---|---|
| | | D.P.M. RELEASED (30 min.incubation in buffer) |
| Blank | | 1264 (2.43) |
| Trypsin-Ficoll (Trypsin equivalent) | 36.0 μg/ml | 2181 (4.20) |
| | 72.0 μg/ml | 2208 (4.25) |
| | 144 μg/ml | 2900 (5.57) |

(Figures in parentheses indicate percentage release of total $^{125}$I)

The caseinolytic activity of the conjugate (FIG. 1) is approximately 40% of that of free enzyme, and the esterolytic activity (Example 9) is increased slightly.

EXAMPLE 7

Pronase-Dextran T40 (II)

Dextran (M.W. 40,000) (1 g) was dissolved in water (100 ml) and reacted with 0.5 g cyanogen bromide as described previously. The solution was adjusted to pH 8.5 and Pronase (100 mg) added. After stirring at 4° C for 16 hours, the material was ultrafiltered and purified by gel filtration as described above. Lyophilisation gave a white powder (0.99 g) containing 51 μg protein/mg. Fibrinolytic activity is shown in Table 8

Table 8.

| Fibrinolytic activity of Pronase-dextran T40(II) in vitro in the presence of buffer and human plasma | | |
|---|---|---|
| | D.P.M. RELEASED (30 min.incubation) | |
| | Buffer | Plasma |
| Blank | 1110 (3.6) | 885 (2.8) |
| Pronase-dextran T40 (II) (Pronase equivalent) 10 μg/ml | 1385 (4.4) | — |
| 25 μg/ml | 1559 (5.0) | 1499 (4.8) |
| 50 μg/ml | 1937 (6.2) | 1770 (5.7) |
| 100 μg/ml | 2334 (7.5) | 2253 (7.2) |

(Figures in parentheses indicate percentage release of total $^{125}$I).

The modification of Pronase with dextran activated to a greater extent than that used in Pronase-dextran T40 (I) also results in a material with fibrinolytic activity which is not inhibited by human plasma.

EXAMPLE 8

Pronase-Dextran T70

Dextran (M.W. 70,000) (2 g) was dissolved in water (200 ml) and activated with cyanogen bromide (0.5 g) at pH 11.00. The pH of the solution was then adjusted to 9.0 and Pronase (250 mg) added. The solution was stirred at 4° C for 16 hours. L-Lysine (1.82 g) was added to neutralise any remaining reactive centres on the dextran and the pH was maintained at 9.5. After stirring for 4 hours at 4° C, the solution was then ultrafiltered (membrane as before) to a volume of 15 ml and purified by gel filtration as described previously. After ultrafiltration and lyophilisation a white powder (1.70 g) was obtained containing 87 μg protein/mg adduct. Fibrinolytic activity is shown in Table 9.

Table 9.

| Effect of Pronase-dextran T70 on fibrinolysis in vitro in the presence of buffer and human plasma | | |
|---|---|---|
| | D.P.M. RELEASED (30 min.incubation) | |
| | Buffer | Plasma |
| Blank | 917 (2.8) | 692 (2.1) |
| Pronase-Dextran T70 8.7 μg/ml | — | 1178 (3.4) |
| (Pronase equivalent) 17.4 μg/ml | 1116 (3.4) | 1385 (4.3) |
| 34.8 μg/ml | 1391 (4.2) | — |

Table 9.-continued

| Effect of Pronase-dextran T70 on fibrinolysis in vitro in the presence of buffer and human plasma | | |
|---|---|---|
| | D.P.M. RELEASED (30 min.incubation) | |
| | Buffer | Plasma |
| 43.5 μg/ml | — | 1615 (5.0) |
| 87 μg/ml | 1948 (6.0) | 1928 (5.9) |
| 174 μg/ml | — | 2811 (8.6) |

(Figures in parentheses indicate percentage release of total $^{125}$I)

Modification of the Pronase with dextran of molecular weight 70,000 reduces the specific fibrinolytic activity of the adduct compared with Example 3, but the abolition of plasma inhibition is still observed.

EXAMPLE 9

Esterolytic Activity of Enzyme Preparations

To give an estimate of peptidolytic activity of the complexes, esterolytic activity was determined using 1mM N-benzoyl arginine ethyl ester (B.A.E.E.) at pH 8.0. 1 B.A.E.E. unit of enzyme will cause an increase in $O.D_{253}{}^{1cm}$ of 0.001 in 1 minute at 25° C.

Table 10.

| | B.A.E.E.UNITS/ mgPROTEIN |
|---|---|
| TRYPSIN | 8185 |
| TRYPSIN-DEXTRAN T40 (II) (Example 4) | 11900 |
| TRYPSIN-FICOLL (Example 6) | 12000 |
| PRONASE | 3350 |
| PRONASE-DEXTRAN T40 (I) (Example 7) | 8280 |

EXAMPLE 10

Caseinolytic Activity of Enzyme Preparations 0.5 ml of the enzyme preparation at various concentrations was incubated at 37° C for 1 hour with 2ml. of 3% w/v. casein and 2.5ml of 0.1M sodium phosphate buffer at pH 7.0. Undigested protein was precipitated with 2ml of 10% w/v trichloroacetic acid and the tyrosine content of the supernatent determined according to the procedure of Lowry et al. [J. Biol. Chem., 193, 265 (1951)]. The optical density is then a measure of the amount of casein solubilised by the enzyme, and hence a measure of caseinolytic activity.

Figure 2:
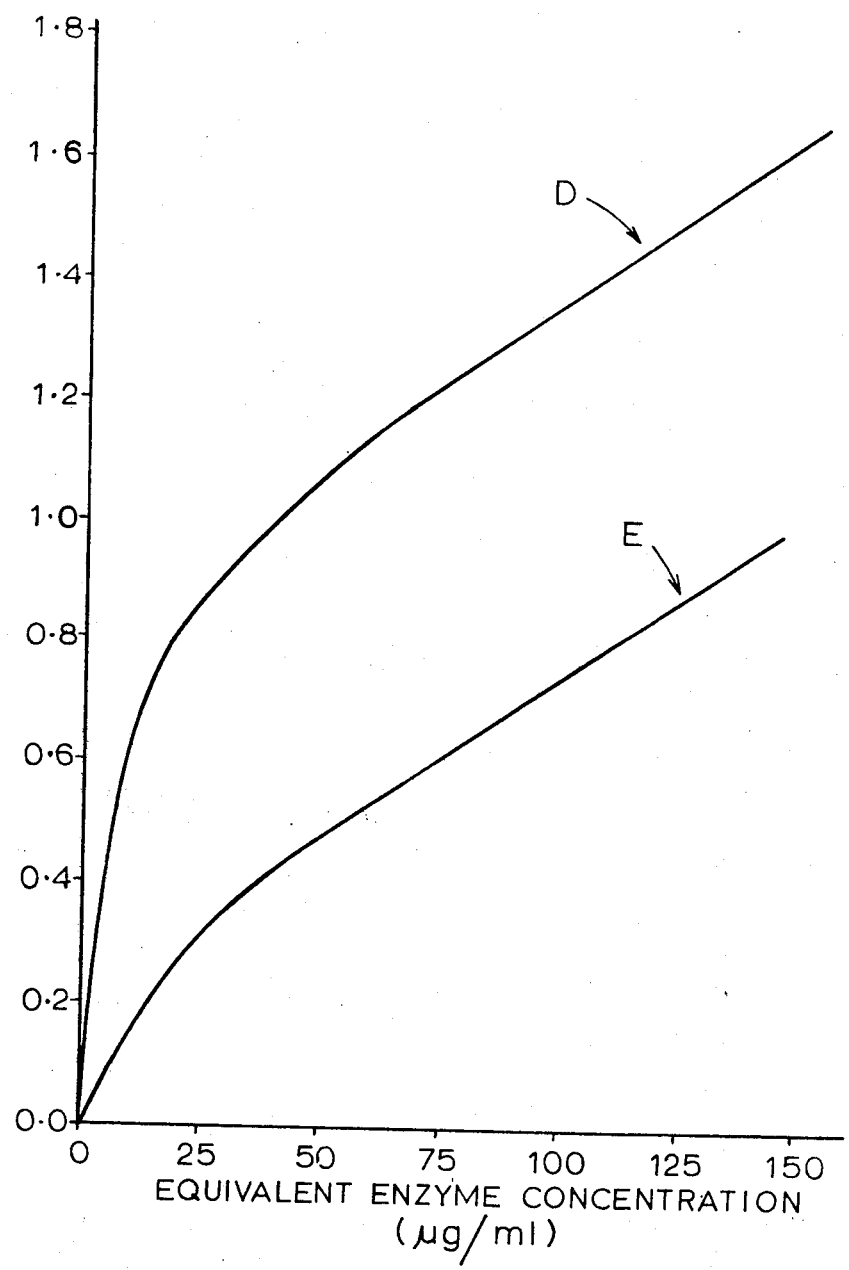

The results for certain enzyme preparations of the invention are shown in FIGS. 1 and 2 wherein the optical density ($O.D._{650nm}{}^{1cm}$) is plotted against the concentration of enzyme or, for the complexes, the equivalent enzyme content of the complex.

In FIG. 1,
curve A represents free trypsin;
curve B represents trypsin-dextran T40 complex (II) of Example 4;
curve C represents trypsin-ficoll complex of Example 6

In FIG. 2.
curve D represents free chymotrypsin;
curve E represents chymotrypsin-dextran T40 complex of Example 5.

We claim:
1. A fibrinolytic pharmaceutical composition in unit dosage form suitable for administration by injection to humans which comprises an amount of a water soluble complex of a proteolytic enzyme sufficient to achieve the desired degree of fibrinolysis on administration to a human and linked covalently to a water-soluble polymeric substance having a molecular weight of from

10,000 to 500,000, said enzyme and said polymeric substance being present in the ratio of 1:2 to 1:50 said composition being substantially free of unreacted enzyme.

2. A composition according to claim 1 wherein the proteolytic enzyme is trypsin, chymotripsin, bromelain, papain, pronase or brinase.

3. A composition according to claim 2 wherein the enzyme is trypsin or pronase.

4. A composition according to claim 1 wherein the water-soluble polymeric substance is a polysaccharide.

5. A composition according to claim 4 wherein the polysaccharide is a dextran.

6. A composition according to claim 4 wherein the polysaccharide is a modified polysaccharide.

7. A composition according to claim 6 wherein the modified polysaccharide is a sucrose-epichlorhydrin copolymer.

8. A composition according to claim 1 in the form of a sealed ampoule containing a predetermined amount of the enzyme complex in a sterile freeze-dried form.

9. A composition according to claim 1 in a form suitable for injection into humans wherein the enzyme complex is dissolved or suspended in sterile or pyrogen-free water or isotonic saline, at a predetermined concentration.

* * * * *